United States Patent [19]
Kihira

[11] Patent Number: 6,010,893
[45] Date of Patent: *Jan. 4, 2000

[54] PROCESS FOR PRODUCING HUMAN MATRILYSIN BY MEANS OF RECOMBINANT DNA

[75] Inventor: Yasunori Kihira, Shiga-ken, Japan

[73] Assignee: Oriental Yeast Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/896,062

[22] Filed: Jul. 17, 1997

Related U.S. Application Data

[63] Continuation of application No. 08/530,984, Sep. 20, 1995, abandoned.

[30] Foreign Application Priority Data

Sep. 30, 1994 [JP] Japan ................................... 6-259576

[51] Int. Cl.$^7$ .............................. C12N 9/64; C07H 21/04
[52] U.S. Cl. .......................... 435/226; 435/212; 435/219; 435/252.3; 435/252.33; 435/320.1; 536/23.1; 536/23.2; 536/23.5
[58] Field of Search ..................................... 435/226, 219, 435/212, 252.3, 252.33, 320.1; 536/23.1, 23.2, 23.4, 23.5

[56] References Cited

U.S. PATENT DOCUMENTS

| 4,652,639 | 3/1987 | Stabinsky | 536/27 |
|---|---|---|---|
| 5,240,831 | 8/1993 | Barnes | 435/69.1 |

OTHER PUBLICATIONS

Sambrook et al. Molecular Cloning: A laboratory Manual, second edition, Cold Spring Harbor Laboratory Press, p. 17.11, 1989.
Grosjean et al. "Preferential codon usage in prokaryotic genes: the optimal codon–anticodon interaction energy and the selective . . . " Gene 18, 199–209, 1982.
Solar et a. "Zinc content of promatrilysin . . . " Biochem. Biophys. Res. comm. 201, 917–923, Jun. 15, 1994.
Barnett et al. "Prod., purif., and charact. of human Matrilysin . . . " Protein Exp. and Pur. 5, 27–46, Feb. 1994.
Crabbe et al. "Biochem. charct. of Matrilysin. Activation . . . " Biochemistry 31, 8500–8507, 1992.
Muller et al. "The collagenase gene family in human consists of at . . . " Biochem. J. 253, 187–192, 1988.
Marti et al. "Molecular charact. of a low–molecular–mass matrix . . . " Biochem. J. 285, 899–905, 1992.
Fujimura et al. "Secretion of recombinant ribonuclease . . . " FEBS 265, 71–74, 1990.
Ye et al, Gene Synthesis and Expression in *E. coli* for Pump a Human Matrix Metalloproteinase, Biochemical and Biophysical Research Communications, vol. 186 No. 1 pp. 143–149, Jul. 5, 1992.
Quantin et al, Pump–1 cDNA Codes for a Protein with Characteristics Similar to those of Classical Collagenase Family Members, Biochemistry, vol. 28, pp. 5327–5334, 1989.
Miyazaki et al, Purification and Characterization of Extracellular Matrix–degrading Metalloproteinase, Matrin (Pump–1), Secreted from Human Rectal Carcinoma Cell Line Cancer Research, vol. 50, pp. 7758–7764, Dec. 15, 1990.
Woessner et al, Purification and Properties of a Small Latent Matrix Metalloproteinase of the Rat Uterus, The Journal of Biological Chemistry, vol. 263 No. 34, pp. 16918–16925 Nov. 15, 1988.
Muller et al, The Collagenase Gene Family in Humans Consists of at least Four Members Biochem. Journal, vol. 253 pp. 187–192, 1988.
Daniele Muller et al, "The Collagenase Gene Family in Humans Consists of at Least Four Members." The Biochemistry Journal, vol. 253, No. 1, Jul. 1988, pp. 187–192.
Dulce Soler et al, "Zinc Contect of Promatrilysin, Matrilysin and the Stromelysin Catalytic Domain." Biochemical and Biophysical Research Communications, vol. 201, No. 2, Jun. 15, 1992, pp. 917–923.
Hiroyuki Yamamoto et al, "Expression of Matrilysin mRNA in Colorectal Adenomas and its Induction By Truncated Fibronectin." vol. 201, No. 2, Jun. 15, 1994, pp. 657–664.
Donald Busiek et al, "The Matrix Metalloprotease Matrilysin (Pump) is Expressed in Developing Human Mononuclear Phagocytes." The Journal of Biological Chemistry, vol. 267, No. 13, May 5, 1992, pp. 9087–9092.
Hans–Peter Marti et al, "Molecular Characterization of a Low–Molecular–Mass Matrix Metalloproteinase Secreted by Glomerular Mesangial Cells as Pump–1." The Biochemical Journal, vol. 285, No. 3, Aug. 1, 1992, pp. 899–905.
Mireille Gaire et al, "Structure and Expression of the Human Gene for the Matrix Metalloproteinase Matrilysin." Journal of Biological Chemistry, vol. 269, No. 3, Jan. 21, 1994, pp. 2032–2040.

*Primary Examiner*—Robert A. Wax
*Assistant Examiner*—Nashaat T. Nashed
*Attorney, Agent, or Firm*—Browdy and Neimark

[57] ABSTRACT

The present invention relates to a process for producing a human matrilysin characterized in that a human promatrilysin is expressed in *E. coli* and secreted into the periplasm thereof; the inclusion body is formed, the human promatrilysin is solubilized with a urea solution, purified and renatured to obtain the active enzyme (active-type matrilysin). By this process, the active human matrilysin can be easily produced from transformed *E. coli*.

13 Claims, 3 Drawing Sheets

FIG. 1

```
EcoRI    MetLysGlnSerThrIleAlaLeuAlaLeuLeuProLeuLeuPheThrProValThr
            10        20  ①    30         40        50        60
(G)AATTCATGAAACAAAGCACTATTGCACTGGCACTCTTACCGTTACTGTTTACCCCTGTGA
       GTACTTTGTTTCGTGATAACGTGACCGTGAGAATGGCAATGACAAATGGGGACACT
                                  ①   -

EcoT141↓      29k-promatrilysin                    PstI
       LysAlaLeuProLeuProGlnGluAlaGlyGlyMetSerGluLeuGlnTrpGluGlnAla
            70    ②    80        90       100       110       120
   CCAAGGCCCTGCCGCTGCCGCAAGAAGCTGGTGGCATGTCTGAACTGCAGTGGGAACAGG
   GGTTCCGGGACGGCGACGGCGTTCTTCGACCACCGTACAGACTTGACGTCACCCTTGTCC
                                  ②   -

GlnAspTyrLeuLysArgPheTyrLeuTyrAspSerGluThrLysAsnAlaAsnSerLeu
           130    ③   140       150       160       170       180
   CACAGGACTATCTGAAGCGTTTTTACCTGTACGACTCTGAAACCAAAAACGCTAATTCTC
   GTGTAATGATAGACTTCGCAAAAATGGACATGCTGAGACTTTGGTTTTTGCGATTAAGAG
                                  ③   -

GluAlaLysLeuLysGluMetGlnLysPhePheGlyLeuProIleThrGlyMetLeuAsn
           190    ④   200       210       220       230       240
   TTGAAGCTAAACTGAAGGAGATGCAGAAATTTTTCGGTCTGCCGATCACCGGTATGCTGA
   AACTTCGATTTGACTTCCTCTACGTCTTTAAAAAGCCAGACGGCTAGTGGCCATACGACT
                                  ④   -
                                                              ↓
       SerArgValIleGluIleMetGlnLysProArgCysGlyValProAspValAlaGluTyr
           250    ⑤   260       270       280       290       300
   ACTCCCGTGTTATCGAAATCATGCAGAAACCGCGTTGTGGTGTTCCGGACGTTGCTGAAT
   TGAGGGCACAATAGCTTTAGTACGTCTTTGGCGCAACACCACAAGGCCTGCAACGACTTA
                                  ⑤   -

19k-matrilysin   (mature type)
       SerLeuPheProAsnSerProLysTrpThrSerLysValValThrTyrArgIleValSer
           310    ⑥   320       330       340       350       360
   ACTCTCTGTTCCCGAACTCTCCGAAATGGACCTCTAAAGTTGTAACCTACCGTATCGTTT
   TGAGAGACAAGGGCTTGAGAGGCTTTACCTGGAGATTTCAACATTGGATGGCATAGCAAA
                                  ⑥   -
                                                          HindIII
       TyrThrArgAspLeuProHisIleThrValAspArgLeuValSerLysAlaLeuAsnMet
           370    ⑦   380       390       400       410       420
   CTTACACCCGTGACCTGCCGCATATCACCGTTGACCGTCTGGTTTCTAAAGCTTTGAACA
   GAATGTGGGCACTGGACGGCGTATAGTGGCAACTGGCAGACCAAAGATTTCGAAACTTGT
                                  ⑦   -

IpnI
       TrpGlyLysGluIleProLeuHisPheArgLysValValTrpGlyThrAlaAspIleMet
           430    ⑧   440       450       460       470       480
   TGTGGGGTAAAGAGATCCCGCTGCATTTTCGTAAAGTTGTATGGGGTACCGCTGACATTA
   ACACCCCATTTCTCTAGGGCGACGTAAAAGCATTTCAACATACCCCATGGCGACTGTAAT
                                  ⑧   -
```

FIG. 2

```
                                                              SmaI
        IleGlyPheAlaArgGlyAlaHisGlyAspSerTyrProPheAspGlyProGlyAsnThr
           490    ⑨  500        510        520        530        540
        TGATCGGTTTCGCTCGTGGTGCTCATGGTGACTCTTACCCGTTCGACGGCCCGGGTAACA
        ACTAGCCAAAGCGAGCACCACGAGTACCACTGAGAATGGGCAAGCTGCCGGGCCCATTGT
                   ⑨-

SphI
        LeuAlaHisAlaPheAlaProGlyThrGlyLeuGlyGlyAspAlaHisPheAspGluAsp
           550    ⑩  560        570        580        590        600
        CCCTGGCGCATGCTTTCGCTCCGGGTACTGGTCTGGGTGGCGACGCACACTTCGACGAAG
        GGGACCGCGTACGAAAGCGAGGCCCATGACCAGACCCACCGCTGCGTGTGAAGCTGCTTC
                   ⑩ -

GluArgTrpThrAspGlySerSerLeuGlyIleAsnPheLeuTyrAlaAlaThrHisGlu
           610    ⑪ 620         630        640        650        660
        ACGAACGTTGGACCGACGGTTCTTCCCTGGGTATCAACTTCCTGTACGCTGCAACTCATG
        TGCTTGCAACCTGGCTGCCAAGAAGGGACCCATAGTTGAAGGACATGCGACGTTGAGTAC
                  ⑪-

LeuGlyHisSerLeuGlyMetGlyHisSerSerAspProAsnAlaValMetTyrProThr
           670    ⑫ 680         690        700        710        720
        AACTGGGTCATTCTCTGGGCATGGGTCATTCTTCCGACCCGAACGCTGTTATGTACCCGA
        TTGACCCAGTAAGAGACCCGTACCCAGTAAGAAGGCTGGGCTTGCGACAATACATGGGCT
                   ⑫ -

TyrGlyAsnGlyAspProGlnAsnPheLysLeuSerGlnAspAspIleLysGlyIleGln
           730    ⑬ 740         750        760        770        780
        CCTACGGTAACGGTGACCCGCAGAACTTCAAACTGTCTCAGGACGATATCAAAGGTATCC
        GGATGCCATTGCCACTGGGCGTCTTGAAGTTTGACAGAGTCCTGCTATAGTTTCCATAGG
                   ⑬ -

LysLeuTyrGlyLysArgSerAsnSerArgLysLys******BamHI
           790    ⑭ 800         810        820          830
        AGAAACTGTACGGTAAACGTTCTAACTCTCGTAAAAAGTAATAGG
        TCTTTGACATGCCATTTGCAAGATTGAGAGCATTTTTCATTATCCCTAG
                   ⑭-
```

PROCESS FOR PRODUCING HUMAN MATRILYSIN BY MEANS OF RECOMBINANT DNA

This application is a continuation of application Ser. No. 08/530,984 filed Sep. 20, 1995 now abandoned.

DETAILED DESCRIPTION OF THE INVENTION

1. Field of the Invention

The present invention relates to a process for producing a human promatrilysin (29k) having a molecular weight of 29,000 and a human mature (activated) matrilysin (19k) having a molecular weight of 19,000. More specifically, the present invention relates to a process for producing matrilysin, which comprises designing a nucleotide sequence of a gene such that the enzyme (matrilysin) is efficiently expressed in a microorganism such as E. coli and secreted, artificially synthesizing such a gene, introducing the gene into the microorganism, separating the matrilysin from the cells, and purifying the resulting matrilysin.

The matrilysin which is obtained in the present invention is useful as a reagent for iatrochemical, biochemical and pharmaceutical investigations, and also useful as a reagent for dispersion of cells to peel off cultured cells of animals from a wall of an instrument or to separate specific cells from tissues of animals. It is particularly useful for dispersing human tissues or cells while maintaining a differentiation activity.

2. Prior Art

An extracellular matrix (ECM) is made of a fibrous structural protein, proteoglycan and the like, and it is indispensable for maintaining and forming tissue. As the main structural protein of ECM, collagen, fibronectin and laminin are known. Cancer cells secrete various proteases such as metalloprotease, serine protease, thiol protease and aspartic protease. Of these, metalloprotease is deemed to participate in hydrolysis of the ECM protein and to be associated with metastasis of cancer cells.

The gene of matrilysin has been also called "pump-1", this name being derived from a putative metalloprotease. This enzyme was first purified from postpartum rat uterus [Woessner J. F., Jr., and Taplin, C. J. (1988), J. Biol. Chem., 263, 16918–16925] and a human rectal carcinoma cell [Miyazaki, K., Hattori, Y., Umenishi, F., Yasumitsu, H., Umeda, M. (1990), Cancer Res. 50, 7758–7764]. Quantin et al. expressed pump-1 cDNA in COS cells [Quantin, B., Murphy, G., and Breathnach, R. (1989), Biochemistry 28, 5327–5334]. Ye, Q., -Z. et al. Highly expressed pump-1 in E. coli [Ye, Q, -Z., Johnson, L. L. and Baragi, V. (1992) Biochem. Biophys. Res. Commun. 186, 143–149]. However, in this method, an inclusion body was formed and the active enzyme could not be obtained.

PROBLEMS TO BE SOLVED BY THE INVENTION

The abovementioned known methods can be hardly said to be industrially satisfactory in the following points. That is, when animal cells are used as a material in producing both the natural and recombinant-type enzymes (The wording "recombinant-type" means hereinafter "produced by means of recombinant DNA".), a costly culture medium is required for culturing the cells, incurring a high production cost. When the recombinant-type enzyme is highly expressed using E. coli, the insoluble inclusion body is formed, and the active enzyme cannot be obtained.

BRIEF DESCRIPTION OF THE DRAWINGS

FIG. 1 is a view showing the nucleotide sequence (SEQ ID NO:1) and the amino acid sequence (SEQ ID NO:2) of a recombinant-type human matrilysin.

FIG. 2 is a view showing the continuation of FIG. 1.

MEANS FOR SOLVING THE PROBLEMS

Figure 3:
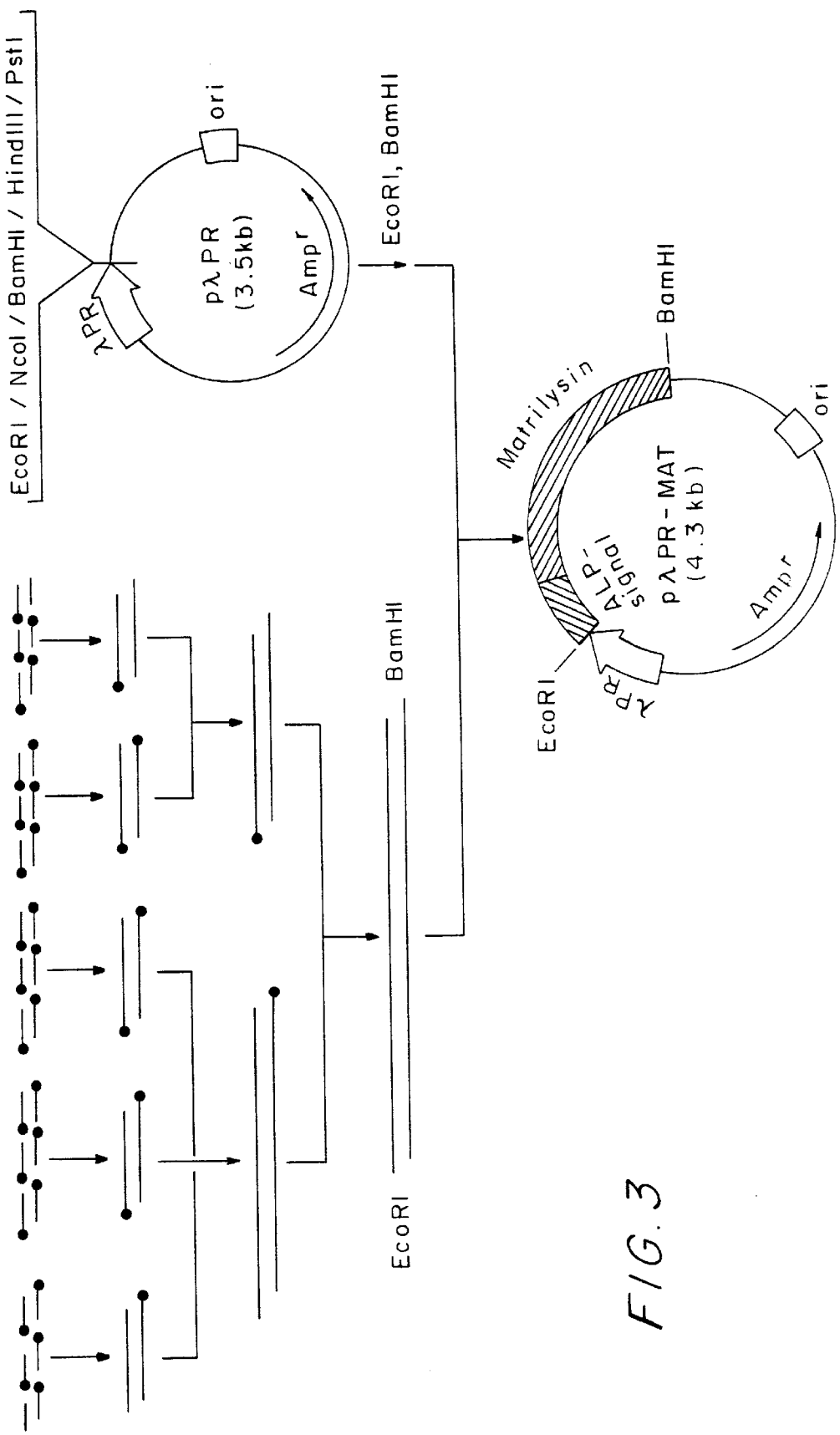
FIG. 3 is a view showing the constructing of the expression plasmid in the present invention.

In order to solve the abovementioned problems, the present inventors have conducted investigations, and have consequently found a process in which an active human matrilysin is efficiently expressed in E. coli. This finding has led to the completion of the present invention.

The process for producing the human matrilysin in the present invention will be described below. The sequence of the human matrilysin gene is already known [Müller, D., Quantin, B., Gesnel, M. C., Millon-Collard, R., Abecassis, J. and Breathnach, R. (1988) Biochem. J. 253, 187–192].

However, even if the human gene is expressed in Escherichia coli (E. coli), the expression efficiency is generally low, and it is quite difficult to produce the gene product on an industrial scale.

Therefore, in order to efficiently express the human matrilysin gene in E. coli, the nucleotide sequence of the human matrilysin gene has been designed using optimum codons of E. coli. At that time, it was presumed that when the mature enzyme is directly expressed, the inclusion body is formed without taking the correct stereostructure. Accordingly, the sequence to express promatrilysin has been employed. Further, to express and secrete matrilysin in E. coli efficiently, a signal peptide of E. coli alkaline phosphatase has been added to the N-terminal side. It has been designed so that the proenzyme formed in the cells is accumulated in the periplasmic region by cleaving the signal peptide with a signal peptidase.

The present inventors have succeeded in actually producing the synthetic gene having the sequence of the human matrilysin gene according to such a design. Further, they have confirmed the selection of the expression vector, the production of a recombinant plasmid in which the synthetic gene is inserted into the expression vector, the formation of a transformant by introducing the recombinant plasmid into a host, the cultivation of the transformant, and the expression of the gene. Still further, they have conducted investigations with respect to the procurement of the active enzyme by solubilization and renaturation of the human matrilysin inclusion body, and have succeeded in it.

The present invention has actually succeeded in expressing the synthetic gene which was so far difficult to be expressed by the gene recombination technique, and has further succeeded for the first time in the production of the active (mature) human matrilysin which could not be obtained so far, by a biochemical method.

DETAILED DESCRIPTION OF THE INVENTION

The present invention will be illustrated more specifically by referring to the following Example.

EXAMPLE 1

(1) Designing of a Human Matrilysin Gene

In order to efficiently express a human matrilysin gene in *E. coli*, the sequence of the human matrilysin gene was designed using optimum codons of *E. coli*. That is, it was not intended to directly express 19k-matrilysin (active type), but a signal peptide of *E. coli* alkaline phosphatase was added to the N-terminal side in order to efficiently express and secrete 29k-promatrilysin (inactive type). For inserting the gene into an expression vector, a recognition sequence of EcoRI was introduced at the N-terminal side and a recognition sequence of BamHI at the C-terminal side, respectively. Recognition sequences of PstI, HindIII, KpnI, SmaI and SphI were introduced into the coding region as restriction enzyme cleavage sites for subcloning which were required to analyze the nucleotide sequence of the synthetic gene.

The nucleotide sequence of the human matrilysin gene is, along with the amino acid sequence thereof, represented by SEQ ID NO:1 of the following Sequence Tables 1 and 2.

TABLE 1

SEQUENCE LISTING:

SEQ ID NO:1
Length of sequence: 825
Type of sequence: nucleic acid
Type of strand: double strand
Topology: linear
Type of sequence: synthetic DNA
Origin:
    Name of organism: human being
Characteristics of sequence:
    Symbol indicating characteristics: CDS
    Location: 6 . . . 818
    Method of determining characteristics: S
    Symbol indicating characteristics: sig peptide
    Location: 6 . . . 68
    Method of determining characteristics: S
Sequence

TABLE 2

```
AATTCATGAAACAAAGCACTATTGCACTGGCACTCTTACCGTTACTGTTTACCCCTGTGACC  62
    MetLysGlnSerThrIleAlaLeuAlaLeuLeuProLeuLeuPheThrProValThr
        -20         -15         -10          -5

AAGGCCCTGCCGCTGCCGCAAGAAGCTGGTGGCATGTCTGAACTGCAGTGGGAACAGGCACAG 125
    LysAlaLeuProLeuProGlnGluAlaGlyGlyMetSerGluLeuGlnTrpGluGlnAlaGln
         1           5          10          15

GACTATCTGAAGCGTTTTTACCTGTACGACTCTGAAACCAAAAACGCTAATTCTCTTGAAGCT 188
    AspTyrLeuLysArgPheTyrLeuTyrAspSerGluThrLysAsnAlaAsnSerLeuGluAla
        20          25          30          35          40

AAACTGAAGGAGATGCAGAAATTTTTCGGTCTGCCGATCACCGGTATGCTGAACTCCCGTGTT 251
    LysLeuLysGluMetGlnLysPhePheGlyLeuProIleThrGlyMetLeuAsnSerArgVal
            45          50          55          60

ATCGAAATCATGCAGAAACCGCGTTGTGGTGTTCCGGACGTTGCTGAATACTCTCTGTTCCCG 314
    IleGluIleMetGlnLysProArgCysGlyValProAspValAlaGluTyrSerLeuPhePro
            65          70          75          80

AACTCTCCGAAATGGACCTCTAAAGTTGTAACCTACCGTATCGTTTCTTACACCCGTGACCTG 377
    AsnSerProLysTrpThrSerLysValValThrTyrArgIleValSerTyrThrArgAspLeu
            85          90          95         100

CCGCATATCACCGTTGACCGTCTGGTTTCTAAAGCTTTGAACATGTGGGGTAAAGAGATCCCG 440
    ProHisIleThrValAspArgLeuValSerLysAlaLeuAsnMetTrpGlyLysGluIlePro
       105         110         115         120

CTGCATTTTCGTAAAGTTGTATGGGGTACCGCTGACATTATGATCGGTTTCGCTCGTGGTGCT 503
    LeuHisPheArgLysValValTrpGlyThrAlaAspIleMetIleGlyPheAlaArgGlyAla
      125         130         135         140         145

CATGGTGACTCTTACCCGTTCGACGGCCCGGGTAACACCCTGGCGCATGCTTTCGCTCCGGGT 566
    HisGlyAspSerTyrProPheAspGlyProGlyAsnThrLeuAlaHisAlaPheAlaProGly
            150         155         160         165

ACTGGTCTGGGTGGCGACGCACACTTCGACGAAGACGAACGTTGGACCGACGGTTCTTCCCTG 629
    ThrGlyLeuGlyGlyAspAlaHisPheAspGluAspGluArgTrpThrAspGlySerSerLeu
            170         175         180         185

GGTATCAACTTCCTGTACGCTGCAACTCATGAACTGGGTCATTCTCTGGGCATGGGTCATTCT 692
    GlyIleAsnPheLeuTyrAlaAlaThrHisGluLeuGlyHisSerLeuGlyMetGlyHisSer
            190         195         200         205

TCCGACCCGAACGCTGTTATGTACCCGACCTACGCTAACGGTGACCCGCAGAACTTCAAACTG 755
    SerAspProAsnAlaValMetTyrProThrTyrGlyAsnGlyAspProGlnAsnPheLysLeu
            210         215         220         225
```

TABLE 2-continued

```
TCTCAGGACGATATCAAAGGTATCCAGAAACTGTACGGTAAACGTTCTAACTCTCGTAAAAAG 818
SerGlnAspAspIleLysGlyIleGlnLysLeuTyrGlyLysArgSerAsnSerArgLysLys
230           235           240           245           250

TAATAGG                                                         825
```

(2) Construction of a Plasmid for Expressing a Human Matrilysin in E. coli

The whole DNA of the human matrilysin gene containing the gene of the signal peptide of E. coli alkaline phosphatase was separated into 28 fragments each having a length of approximately 50 bases as shown in FIGS. 1 and 2. Each of these was synthesized by a DNA automatic synthesizer. The DNA fragments were ligated with a T4DNA ligase according to the order shown in FIG. 3 to prepare an artificially synthetic gene.

pλPR having λPR promotor and EcoRI, NcoI, BamHI, HindIII and PstI sites as cloning sites was used as an expression vector. This expression vector was cleaved with EcoRI and BamHI, and the synthetic gene of the human matrilysin was inserted thereinto to prepare pλPR-MAT. The ligation reaction was conducted at 14° C. for 16 hours using T4DNA ligase. E. coli N99cI+ (F-, strA, galK2λ-, IN (rrnD–rrnE)1) was transformed by using the reaction product. The thus-obtained plasmid of the transformant strain was separated by an alkali-SDS method, and the insertion of the intended gene was confirmed by analysis with the restriction enzymes. Subsequently, the transformation of E. coli N4830-1 [F-suohis-, ilv-, galK-, (chlD-pgl), (λ, Bam, N+, cI857, Hl)] was conducted again.

(3) Culturing of the Transformant Strain

E. coli N4830-1 transformed by using plasmid pλPR-MAT was named Escherichia coli N4830-1/pλPR-MAT, and it has been deposited at the National Institute of Bioscience and Human Technology of the Agency of Industrial Science and Technology under FERM BP-4794. This transformant strain was cultured in LB medium containing 50 μg/ml of ampicillin at 30° C. for 16 hours. The thus-obtained strain solution was inoculated in an amount of 3% into LB medium containing 50 μg/ml of ampicillin, and cultured at 30° C. for 6 hours, and then at 34° C. or 42° C. for from 1 to 4 hours.

(4) Purification of Matrilysin and Properties Thereof

When the expression of matrilysin was induced at 34° C., a relatively small amount of 29k-promatrilysin was expressed in the soluble state. When the expression was induced at 42° C., a large amount of 31k-prepromatrilysin containing the signal peptide was expressed in the insoluble state. With respect to 31k-prepromatrilysin, the purification and renaturation were conducted by the following method to obtain the active enzyme.

The cells (cell pellet) were suspended in 50 mM Tris-HCl buffer (pH 7.5) containing 150 mM NaCl and 0.5 mM EDTA in a volume which was three times that of the cell pellet, and disrupted by a Dyno-Mill. The thus-disrupted cells were centrifuged at 4° C. for 20 minutes at 15,000 rpm, and separated into supernatant and precipitate (when the soluble 29k-promatrilysin was expressed, it was purified from this supernatant). The inclusion body was prepared from the obtained precipitate by the following treatment. First, the precipitate was suspended in a 1 M sucrose solution, and the suspension was centrifuged at 10,000 rpm for 15 minutes to obtain the precipitate. The precipitate was suspended in a solution containing 2% Triton X-100 and 10 mM EDTA, and the suspension was stirred at 4° C. for 18 hours. This suspension was centrifuged at 10,000 rpm for 15 hours to obtain a precipitate. The thus-obtained precipitate was washed with a 10 mM EDTA solution three times to obtain the inclusion body. The thus-obtained inclusion body was dissolved in 10 mM Tris-HCl buffer (pH 7.5) containing 8 M urea and 0.01% Brij35 (buffer A), and applied to an SP-Sepharose column equilibrated with buffer A. The intended protein was adsorbed on the SP-Sepharose column under such conditions. After the column was fully washed with buffer A, the protein was eluted with a linear concentration gradient of NaCl from 0 M to 0.5 M. The intended protein fraction was concentrated with a Diaflow-YM-10 membrane. The concentrated sample was subjected to molecular sieve chromatography using a Superdex 200 column equilibrated with buffer A. By this procedure, 31k-prepromatrilysin containing the signal peptide was purified.

The fraction containing the 31k-prepromatrilysin obtained by the molecular sieve chromatography was collected, and dialyzed against 50 mM Tris-HCl buffer (pH 7.5) containing 0.5 M NaCl, 0.01% Brij 35 and 1 mM EDTA at 4° C. for 17 hours. Then, the 31k-prepromatrilysin was renatured in the soluble state.

When the thus-obtained 31k-prepromatrilysin was incubated in the presence of 0.1 mM $ZnCl_2$ and 10 mM $CaCl_2$ at 37° C., this 31k-prepromatrilysin was converted into 29k-promatrilysin in an approximate 1 hour, and into 19k-matrilysin in approximate 17 hours.

EFFECTS OF THE INVENTION

In accordance with the process of the present invention, a high-purity human matrilysin can be easily produced on an industrial scale without the need for culturing animal cells which incurs high cost.

What is claimed is:

1. A process for producing a soluble human promatrilysin comprising:

(a) preparing a nucleotide sequence for expressing human promatrilysin of 29k by a method comprising the following steps in any order:
   (i) changing some codons of the nucleotide sequence of human promatrilysin to codons suitable for *Escherichia coli* without causing a change in the amino acids to obtain nucleotide sequence SEQ ID NO:1;
   (ii) adding the nucleotide sequence of the signal peptide of *Escherichia coli* alkaline phosphatase at the 5'-end; and
   (iii) adding restriction sites at the 5'- and 3'-ends;

(b) inserting the nucleotide sequence represented by SEQ ID NO:1 obtained in step (a) into a vector;

(c) transforming *Escherichia coli* with the recombinant vector obtained in step (b);

(d) culturing the transformant obtained in step (c) at a temperature at which neither 29k-promatrilysin nor 31k-prepromatrilysin is expressed;

(e) inducing the expression of 29k-promatrilysin at a temperature slightly higher than the temperature in step (d), said slightly higher temperature being such that 29k-promatrilysin is expressed but 31k-prepromatrilysin is substantially not expressed;

(f) collecting the cells;

(g) disrupting the cells in a buffer solution and centrifuging the buffer solution containing the disrupted cells; and (h) recovering 29k-promatrilysin from the supernatant formed by the centrifugation.

2. The process according to claim 1 wherein the vector in step (b) is plasmid pλPR, the *Escherichia coli* in step (c) is *Escherichia coli* N4830-1, and the temperature in step (d) is 30° C. and the temperature in step (e) is 34° C.

3. Recombinant vector pλPR-MAT.

4. *Escherichia coli* N4830-1/pλPR-MAT, FERM BP-4794.

5. An isolated nucleotide sequence comprising the nucleotide sequence of from base No. 69 to base No. 818 in SEQ ID NO:1.

6. The isolated nucleotide sequence represented by SEQ ID NO:1.

7. A process for producing a soluble human promatrilysin comprising:

(a) preparing a nucleotide sequence for expressing human promatrilysin of 29k by a method comprising the following steps in any order:

(i) changing some codons of the nucleotide sequence or human promatrilysin to codons suitable for *Escherichia coli* without causing a change in the amino acids to obtain the nucleotide sequence represented by SEQ ID NO:1;

(ii) adding the nucleotide sequence of the signal peptide of *Escherichia coli* alkaline phosphatase at the 5'-end; and (iii) adding restriction sites at the 5'- and 3'-ends;

(b) inserting the nucleotide sequence represented by SEQ ID NO:1 obtained in step (a) into a vector;

(c) transforming *Escherichia coli* with the recombinant vector obtained in step (b);

(d) culturing the transformant obtained in step (c) at a temperature at which neither 29k-promatrilysin nor 31k-prepromatrilysin is expressed;

(e) inducing the expression of 31k-prepromatrilysin at a higher temperature than the temperature in step (d), said higher temperature being a temperature at which 31k-prepromatrilysin is expressed by 29k-promatrilysin is substantially not expressed;

(f) collecting the cells;

(g) disrupting the cells in a buffer solution and centrifuging the buffer solution containing the disrupted cells;

(h) collecting the precipitate formed by the centrifugation;

(i) obtaining the inclusion body of 31k-prepromatrilysin from the precipitate;

(j) dissolving the inclusion body in a buffer solution containing a denaturing agent;

(k) purifying 31k-prepromatriloysin formed in step (j) using chromatography;

(l) subjecting the purified 31k-prepromatrilysin containing fraction to at least one treatment selected from the group consisting of dialysis treatment and dilution treatment;

(m) recovering the resulting soluble 31k-prepromatrilysin;

(n) incubating the 31k-prepromatrilysin in a solution containing metallic ions at a temperature at which cutting is caused by autocatalytic reaction; and (o) recovering the 29k-promatrilysin formed.

8. The process according to claim 7 wherein the vector in step (b) is plasmid p pR, the *Escherichia coli* in step (c) is *Escherichia coli* N4839-1, the temperature in step (d) is 30° C., and the temperature in step (e) is 42° C.

9. The process according to claim 7 wherein the denaturing agent in step (j) is urea, the chromatography in step (k) is ion exchange chromatography and molecular sieve chromatography, the at least one treatment in step (l) is dialysis treatment, the solution containing metallic ions in step (n) is a solution containing $ZnCl_2$ and $CaCl_2$, and the temperature in step (n) is 37° C.

10. A process for producing 19k human matrilysin comprising:

(a) preparing a nucleotide sequence for expressing human promatrilysin of 29k by a method comprising the following steps in any order:

(i) changing some codons of the nucleotide sequence of human promatrilysin to codons suitable for *Escherichia coli* without causing a change in the amino acids to obtain nucleotide sequence SEQ ID NO:1;

(ii) adding the nucleotide sequence of the signal peptide of *Escherichia coli* alkaline phosphatase at the 5'-end; and (iii) adding restriction sites at the 5'- and 3'-ends;

(b) inserting the nucleotide sequence represented by SEQ ID NO:1 obtained in step (a) into a vector;

(c) transforming *Escherichia coli* with the recombinant vector obtained in step (b);

(d) culturing the transformant obtained in step (c) at a temperature at which neither 29k-promatrilysin nor 31k-prepromatrilysin is expressed;

(e) inducing the expression of 29k-promatrilysin at a temperature slightly higher than the temperature in step (d), said slightly higher temperature being such that 29k-promatrilysin is expressed but 31k-prepromatrilysin is substantially not expressed;

(f) collecting the cells;

(g) disrupting the cells in a buffer solution and centrifuging the buffer solution containing the disrupted cells;

(h) recovering 29k-promatrilysin from the supernatant formed by the centrifugation; and (i) incubating the 29-k promatrilysin in a solution containing metallic ions at a temperature at which cutting is effected by autocatalytic reaction; and (j) recovering the 19-k matrilysin formed.

11. The process according to claim 10 wherein the solution containing metallic ions is a solution containing $ZnCl_2$ and $CaCl_2$, and the temperature is 37° C.

12. A process for producing 19k- human matrilysin comprising:

(a) preparing a nucleotide sequence for expressing human promatrilysin of 29k by a method comprising the following steps in any order:

(i) changing some codons of the nucleotide sequence or human promatrilysin to codons suitable for *Escherichia coli* without causing a change in the amino acids to obtain the nucleotide sequence represented by SEQ ID NO:1;

(ii) adding the nucleotide sequence of the signal peptide of *Escherichia coli* alkaline phosphatase at the 5'-end; and (iii) adding restriction sites at the 5'- and 3'-ends;

(b) inserting the nucleotide sequence represented by SEQ ID NO:1 obtained in step (a) into a vector;

(c) transforming *Escherichia coli* with the recombinant vector obtained in step (b);

(d) culturing the transformant obtained in step (c) at a temperature at which neither 29k-promatrilysin nor 31k-prepromatrilysin is expressed;

(e) inducing the expression of 31k-prepromatrilysin at a higher temperature than the temperature in step (d), said higher temperature being a temperature at which 31k-prepromatrilysin is expressed but 29k-promatrilysin is substantially not expressed;

(f) collecting the cells;

(g) disrupting the cells in a buffer solution and centrifuging the buffer solution containing the disrupted cells;

(h) collecting the precipitate formed by the centrifugation;

(i) obtaining the inclusion body of 31k-prepromatrilysin from the precipitate;

(j) dissolving the inclusion body in a buffer solution containing a denaturing agent;

(k) purifying 31k-prepromatriloysin formed in step (j) using chromatography;

(l) subjecting the purified 31k-prepromatrilysin containing fraction to at least one treatment selected from the group consisting of dialysis treatment and dilution treatment;

(m) recovering the resulting soluble 31k-prepromatrilysin;

(n) incubating the 31k-prepromatrilysin in a solution containing metallic ions at a temperature at which cutting is caused in the prodomain thereof by autocatalytic reaction until 19k-matrilysin is produced; and (o) recovering the 19k-matrilysin formed.

13. The process according to claim 12 wherein the solution containing metallic ions is a solution containing $ZnCl_2$ and $CaCl_2$, and the temperature is 37° C.

* * * * *

SEQUENCE LISTING (1) GENERAL INFORMATION:

(iii) NUMBER OF SEQUENCES: 2

(2) INFORMATION FOR SEQ ID NO:1:

-continued (i) SEQUENCE CHARACTERISTICS:
    (A) LENGTH: 825 base pairs
    (B) TYPE: nucleic acid
    (C) STRANDEDNESS: double
    (D) TOPOLOGY: linear (ii) MOLECULE TYPE: cDNA (ix) FEATURE:
    (A) NAME/KEY: CDS
    (B) LOCATION: 6..818

(xi) SEQUENCE DESCRIPTION: SEQ ID NO:1:

```
AATTC ATG AAA CAA AGC ACT ATT GCA CTG GCA CTC TTA CCG TTA CTG        47
      Met Lys Gln Ser Thr Ile Ala Leu Ala Leu Leu Pro Leu Leu
      1               5                   10

TTT ACC CCT GTG ACC AAG GCC CTG CCG CTG CCG CAA GAA GCT GGT GGC      95
Phe Thr Pro Val Thr Lys Ala Leu Pro Leu Pro Gln Glu Ala Gly Gly
15                  20                  25                  30

ATG TCT GAA CTG CAG TGG GAA CAG GCA CAG GAC TAT CTG AAG CGT TTT     143
Met Ser Glu Leu Gln Trp Glu Gln Ala Gln Asp Tyr Leu Lys Arg Phe
                35                  40                  45

TAC CTG TAC GAC TCT GAA ACC AAA AAC GCT AAT TCT CTT GAA GCT AAA     191
Tyr Leu Tyr Asp Ser Glu Thr Lys Asn Ala Asn Ser Leu Glu Ala Lys
            50                  55                  60

CTG AAG GAG ATG CAG AAA TTT TTC GGT CTG CCG ATC ACC GGT ATG CTG     239
Leu Lys Glu Met Gln Lys Phe Phe Gly Leu Pro Ile Thr Gly Met Leu
        65                  70                  75

AAC TCC CGT GTT ATC GAA ATC ATG CAG AAA CCG CGT TGT GGT GTT CCG     287
Asn Ser Arg Val Ile Glu Ile Met Gln Lys Pro Arg Cys Gly Val Pro
    80                  85                  90

GAC GTT GCT GAA TAC TCT CTG TTC CCG AAC TCT CCG AAA TGG ACC TCT     335
Asp Val Ala Glu Tyr Ser Leu Phe Pro Asn Ser Pro Lys Trp Thr Ser
95                  100                 105                 110

AAA GTT GTA ACC TAC CGT ATC GTT TCT TAC ACC CGT GAC CTG CCG CAT     383
Lys Val Val Thr Tyr Arg Ile Val Ser Tyr Thr Arg Asp Leu Pro His
                115                 120                 125

ATC ACC GTT GAC CGT CTG GTT TCT AAA GCT TTG AAC ATG TGG GGT AAA     431
Ile Thr Val Asp Arg Leu Val Ser Lys Ala Leu Asn Met Trp Gly Lys
            130                 135                 140

GAG ATC CCG CTG CAT TTT CGT AAA GTT GTA TGG GGT ACC GCT GAC ATT     479
Glu Ile Pro Leu His Phe Arg Lys Val Val Trp Gly Thr Ala Asp Ile
        145                 150                 155

ATG ATC GGT TTC GCT CGT GGT GCT CAT GGT GAC TCT TAC CCG TTC GAC     527
Met Ile Gly Phe Ala Arg Gly Ala His Gly Asp Ser Tyr Pro Phe Asp
160                 165                 170

GGC CCG GGT AAC ACC CTG GCG CAT GCT TTC GCT CCG GGT ACT GGT CTG     575
Gly Pro Gly Asn Thr Leu Ala His Ala Phe Ala Pro Gly Thr Gly Leu
175                 180                 185                 190

GGT GGC GAC GCA CAC TTC GAC GAA GAC GAA CGT TGG ACC GAC GGT TCT     623
Gly Gly Asp Ala His Phe Asp Glu Asp Glu Arg Trp Thr Asp Gly Ser
                195                 200                 205

TCC CTG GGT ATC AAC TTC CTG TAC GCT GCA ACT CAT GAA CTG GGT CAT     671
Ser Leu Gly Ile Asn Phe Leu Tyr Ala Ala Thr His Glu Leu Gly His
            210                 215                 220

TCT CTG GGC ATG GGT CAT TCT TCC GAC CCG AAC GCT GTT ATG TAC CCG     719
Ser Leu Gly Met Gly His Ser Ser Asp Pro Asn Ala Val Met Tyr Pro
        225                 230                 235

ACC TAC GGT AAC GGT GAC CCG CAG AAC TTC AAA CTG TCT CAG GAC GAT     767
Thr Tyr Gly Asn Gly Asp Pro Gln Asn Phe Lys Leu Ser Gln Asp Asp
240                 245                 250

ATC AAA GGT ATC CAG AAA CTG TAC GGT AAA CGT TCT AAC TCT CGT AAA     815
Ile Lys Gly Ile Gln Lys Leu Tyr Gly Lys Arg Ser Asn Ser Arg Lys
```

```
255                 260                 265                 270

AAG TAATAGG                                                                    825
Lys (2) INFORMATION FOR SEQ ID NO:2:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Gln Ser Thr Ile Ala Leu Ala Leu Leu Pro Leu Leu Phe Thr
1               5                   10                  15

Pro Val Thr Lys Ala Leu Pro Leu Pro Gln Glu Ala Gly Gly Met Ser
                20                  25                  30

Glu Leu Gln Trp Glu Gln Ala Gln Asp Tyr Leu Lys Arg Phe Tyr Leu
            35                  40                  45

Tyr Asp Ser Glu Thr Lys Asn Ala Asn Ser Leu Glu Ala Lys Leu Lys
        50                  55                  60

Glu Met Gln Lys Phe Phe Gly Leu Pro Ile Thr Gly Met Leu Asn Ser
65                  70                  75                  80

Arg Val Ile Glu Ile Met Gln Lys Pro Arg Cys Gly Val Pro Asp Val
                85                  90                  95

Ala Glu Tyr Ser Leu Phe Pro Asn Ser Pro Lys Trp Thr Ser Lys Val
            100                 105                 110

Val Thr Tyr Arg Ile Val Ser Tyr Thr Arg Asp Leu Pro His Ile Thr
        115                 120                 125

Val Asp Arg Leu Val Ser Lys Ala Leu Asn Met Trp Gly Lys Glu Ile
130                 135                 140

Pro Leu His Phe Arg Lys Val Val Trp Gly Thr Ala Asp Ile Met Ile
145                 150                 155                 160

Gly Phe Ala Arg Gly Ala His Gly Asp Ser Tyr Pro Phe Asp Gly Pro
                165                 170                 175

Gly Asn Thr Leu Ala His Ala Phe Ala Pro Gly Thr Gly Leu Gly Gly
            180                 185                 190

Asp Ala His Phe Asp Glu Asp Glu Arg Trp Thr Asp Gly Ser Ser Leu
        195                 200                 205

Gly Ile Asn Phe Leu Tyr Ala Ala Thr His Glu Leu Gly His Ser Leu
        210                 215                 220

Gly Met Gly His Ser Ser Asp Pro Asn Ala Val Met Tyr Pro Thr Tyr
225                 230                 235                 240

Gly Asn Gly Asp Pro Gln Asn Phe Lys Leu Ser Gln Asp Asp Ile Lys
                245                 250                 255

Gly Ile Gln Lys Leu Tyr Gly Lys Arg Ser Asn Ser Arg Lys Lys
                260                 265                 270
```